(12) United States Patent
Massad

(10) Patent No.: US 8,926,327 B2
(45) Date of Patent: Jan. 6, 2015

(54) DENTAL DEVICE AND METHOD OF USE THEREOF

(75) Inventor: Joseph J. Massad, Tulsa, OK (US)

(73) Assignee: Global Dental Impression Trays, Inc., Tulsa, OK (US)

( * ) Notice: Subject to any disclaimer, the term of this patent is extended or adjusted under 35 U.S.C. 154(b) by 0 days.

(21) Appl. No.: 13/426,147

(22) Filed: Mar. 21, 2012

(65) Prior Publication Data

US 2012/0178045 A1     Jul. 12, 2012

Related U.S. Application Data

(63) Continuation-in-part of application No. 29/404,327, filed on Oct. 19, 2011, now Pat. No. Des. 663,425, and a continuation-in-part of application No. 12/108,100, filed on Apr. 23, 2008, now abandoned.

(60) Provisional application No. 60/986,149, filed on Nov. 7, 2007.

(51) Int. Cl.
*A61C 13/107* (2006.01)
*A61C 13/271* (2006.01)

(52) U.S. Cl.
CPC ............. *A61C 13/0001* (2013.01); *A61C 13/26* (2013.01)
USPC .......................... 433/213; 433/171; 433/212.1

(58) Field of Classification Search
CPC .... A61C 13/00; A61C 13/0001; A61C 13/08; A61C 13/087; A61C 13/081
USPC .......................... 433/229, 218–219, 215, 213, 433/202.1–212.1, 171, 191, 197, 6, 214
See application file for complete search history.

(56) References Cited

U.S. PATENT DOCUMENTS

| | | |
|---|---|---|
| 1,507,024 A | 9/1924 | Monson |
| 2,697,278 A | 12/1954 | Kohler |

(Continued)

FOREIGN PATENT DOCUMENTS

| | | |
|---|---|---|
| DE | 4323074 | 1/1995 |
| WO | WO2008064904 A1 * | 6/2008 |

OTHER PUBLICATIONS

Machine Translation of WO 2008/064904. Accessed at EPO website May 1, 2014.*

(Continued)

*Primary Examiner* — Edward Moran
(74) *Attorney, Agent, or Firm* — Head, Johnson & Kachigian, P.C.

(57) ABSTRACT

A unitary dental device constructed from a suitable thermoplastic or thermosetting material allowing the dental device to be heat molded by a dental practitioner sitting chair side to a patient. The dental device includes a single-piece, shell-like analog having the appearance of contoured, individual teeth. The dental device may also include a pair of posterior tooth extensions in order to create a custom buccal corridor specifically adapted for the patient. A connection bridge uniformly joins the proximal contact areas intermediate of adjacent teeth to form the unitary shell-like analog. The dental device may be temporarily affixed in the patient's mouth to allow both the patient and the dental practitioner to preview chair side the look of a final smile design with a fully-fabricated dental prosthesis. Once the patient and dentist are satisfied with the particular tooth selection and characterization, the dental prosthesis can be fabricated from the dental device.

23 Claims, 6 Drawing Sheets

(56) References Cited

U.S. PATENT DOCUMENTS

| | | | |
|---|---|---|---|
| 3,763,564 | A | 10/1973 | Petrelli et al. |
| 4,380,435 | A | 4/1983 | Raeder et al. |
| 5,635,545 | A * | 6/1997 | Oxman et al. ............... 523/115 |
| 5,852,248 | A * | 12/1998 | Chadwick ...................... 75/228 |
| 5,951,291 | A | 9/1999 | Albert et al. |
| 7,357,637 | B2 | 4/2008 | Liechtung |
| 7,520,747 | B2 | 4/2009 | Stonisch |
| 8,043,092 | B2 | 10/2011 | Stonisch |
| 2004/0241614 | A1 * | 12/2004 | Goldberg et al. .......... 433/202.1 |
| 2005/0227204 | A1 * | 10/2005 | Hauck .......................... 433/218 |
| 2006/0076698 | A1 * | 4/2006 | Hamlin .......................... 264/16 |
| 2006/0286502 | A1 | 12/2006 | Shor |
| 2007/0009855 | A1 * | 1/2007 | Stonisch ...................... 433/215 |
| 2007/0298381 | A1 * | 12/2007 | Collodoro ..................... 433/215 |
| 2008/0044793 | A1 * | 2/2008 | White ........................... 433/171 |
| 2009/0042161 | A1 * | 2/2009 | Jodaikin et al. ................ 433/80 |
| 2011/0033815 | A1 | 2/2011 | Stonisch |

OTHER PUBLICATIONS

Braun et al. "The form of the human dental arch". The Angle Orthodontist Volumner 68, No. 1, 1998.*

Ahmad. "Protocols for Predictrable Aesthetic Dental Restorations." 2006. p. 157.

* cited by examiner

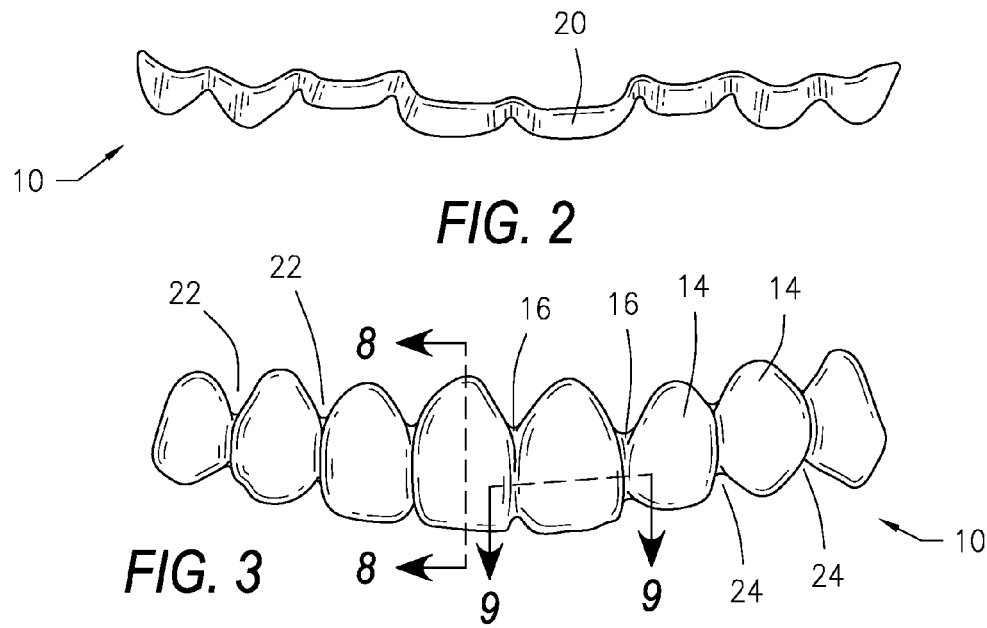
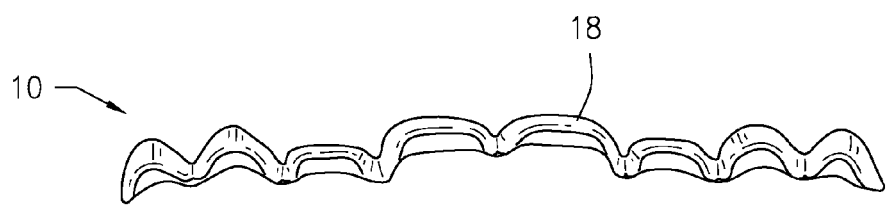
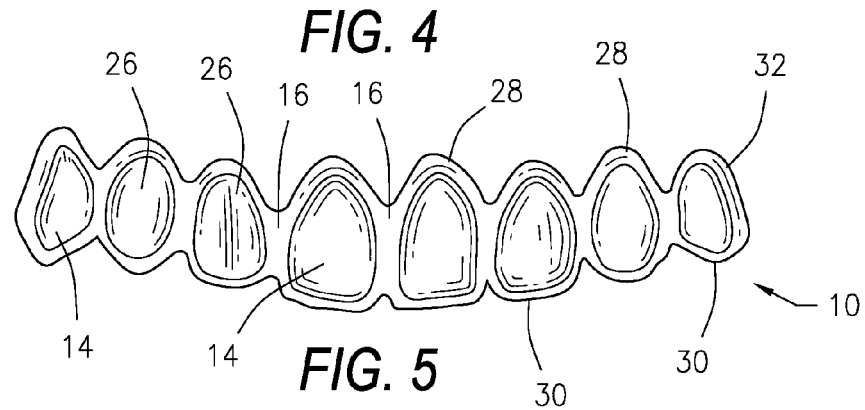
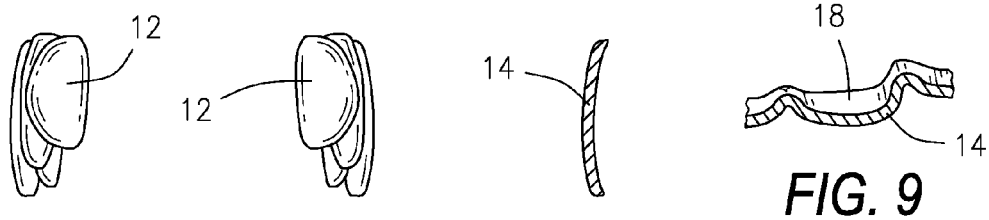

DENTAL DEVICE AND METHOD OF USE THEREOF

CROSS-REFERENCE TO RELATED APPLICATIONS

This application is a continuation-in-part of U.S. Design patent application Ser. No. 29/404,327, filed Oct. 19, 2011, and a continuation-in-part of U.S. patent application Ser. No. 12/108,100, filed Apr. 23, 2008, which claims priority to U.S. Provisional Patent Application Ser. No. 60/986,149, filed Nov. 7, 2007, each of which are incorporated herein by reference in its entirety.

BACKGROUND OF THE INVENTION

1. Field of the Invention

This invention relates to a dental device and a method of thereof, and more particularly, to a unitary dental device having a shell-like analogue with the appearance of individual maxillary or mandibular teeth and to a method of constructing a dental prosthesis using the dental device, which facilitates rapid, accurate and customized set-up of the dental prosthesis specifically adapted to individual patient needs.

2. Description of the Related Art

The laboratory fabrication of complete and partial dentures and in total crowning necessitates a balance between artistic creativity and scientific principles. Successful laboratory technicians develop these skills over many years of trial and improvement. Though much of prosthetic construction involves historically proven, scientifically honed procedures, current methods are overwhelmingly artistic in nature and therefore remarkably time consuming. Of particular concern is the need to specifically manipulate each individual denture and or prosthetic tooth during the tooth set-up procedures. Individual tooth set-up is biomechanically demanding, time consuming and unique to each patient involved.

It is therefore desirable to provide a dental device comprising a unitary shell-like analogue that is heat moldable and has the appearance of individual maxillary or mandibular teeth.

It is further desirable to provide a dental device and method of use thereof that allow both a dental practitioner and a patient to select at chair side a particular tooth mode, shape and size that most appropriately fit the patient's face.

It is still further desirable to provide a dental device and method of use thereof that procedurally enhance and simplify the demanding and time consuming laboratory fabrication process of constructing a complete dental prosthesis.

It is yet further desirable to provide a dental device and method of use thereof, which streamline dental prosthesis construction by facilitating rapid, accurate and individualized setup of the dental prosthesis.

It is still further desirable to provide a dental device that can be milled into an anatomically accurate composite shell-like analogue using CAD/CAM dental technologies.

It is yet further desirable to provide a dental device designed to be set into a dental prosthesis as a complete unit to greatly expediting and simplifying setup of dental teeth and dentures.

It is still further desirable to provide a dental device and method of use thereof that permit easy development of the dental arch form allowing the dental device to be readily adapted to individual patient needs.

It is yet further desirable to provide a dental device and method of use thereof, which permit manipulation of each individual tooth allowing for customized arrangements of the denture teeth, including the incorporation of overlaps, vertical discrepancies, horizontal discrepancies, diastemata, facial-lingual angular variation and mesial-distal angular variation.

It is still further desirable to provide a dental device and method of use thereof that facilitate the creation of anatomically realistic and hygienically favorable papilla forms.

It is yet further desirable to provide a dental device and method of use thereof that include a pair of posterior tooth extensions to create a custom buccal corridor specifically adapted for the individual patient.

BRIEF SUMMARY OF THE INVENTION

In general, in a first aspect, the invention relates to a dental device constructed of a unitary, shell-like analogue having individual teeth unified using connection bridges. The shell-like analogue is made of a single piece of a thermoplastic material, and is pliable when sufficiently heated allowing a dental practitioner to form a dental arch. For example, the shell-like analogue may become pliable when heated to between about 100° F. and 150° F., namely about 140° F. Each of the teeth is adjustable horizontally, vertically and angularly with respect to each other by the chair side dental practitioner. The connection bridges are intermediate of the proximal contact areas of the teeth, thereby permitting overlap, vertical discrepancies, horizontal discrepancies, diastemata, facial-lingual angular variation and/or mesial-distal angular variation of each of the teeth with respect to each other.

The thermoplastic material may be any dental- or medical-grade thermoplastic material suitable for use in the human mouth, such as polyethylene, polystyrene or polypropylene. By way of example, the thermoplastic material may be composed of approximately 70% to approximately 90% W/W polystyrene with 1,3-butadien-e polymer and approximately 10% to approximately 20% W/W polystyrene, or composed of at least 96% by weight of the polystyrene and no more than 3% by weight of a mineral oil. Additionally, the thermoplastic material may include a colorant compound.

The dental device is sized to be placed over existing teeth without causing the patient's lip to protrude unnaturally, and the dental device may have a thickness of between approximately 0.020 inches and approximately 0.080 inches. In addition, each of the teeth of shell-like analogue may be contoured on a lingual portion to form a channel generally spanning between an apical tip and a distal tip of each of the teeth. The teeth of the shell-like analogue may be either mandibular or maxillary teeth, and include at least anterior teeth. Each of the teeth includes a cervical edge and an incisal edge forming cervical embrasures and incisal embrasures of the shell-like analogue. The cervical embrasures of the shell-like analogue allow the practitioner to form anatomically accurate papilla.

Moreover, the dental device may further include at least one or a pair of posterior tooth extensions. Each extension has a curvature and contour mimicking posterior mandibular or maxillary teeth allowing the posterior tooth to be positioned by manipulating the tooth extensions to show more or less posterior tooth. The tooth extensions are adjustable along the anterior-posterior incline and/or the buccal-lingual dimension in order to form a custom buccal corridor specifically adaptable to an individual patient.

In general, in a second aspect, the invention relates to a method of constructing a dental prosthesis. The method includes the steps of fitting a dental device to a patient's oral cavity, and then setting the dental device as a unit into a dental prosthesis. The dental device is a unitary, shell-like analogue having individual teeth with connection bridges intermediate of proximal contact areas of the teeth. The step of fitting the dental device can further include forming a dental arch by heating the dental device and bending the shell-like analogue of the dental device to match or improve the patient's dental arch. In addition, the step of fitting the dental device may include arranging the teeth of the shell-like analogue by manipulating each of the teeth. The teeth may be manipulated by overlap, vertical discrepancies, horizontal discrepancies, diastemata, facial-lingual angular variation or mesial-distal angular variation of the teeth. Moreover, the step of fitting the dental device may include adjusting a pair of tooth extensions to create a custom buccal corridor specifically adapted for the individual patient. The buccal corridor may be created by heating each of the tooth extensions and altering the anterior-posterior incline and/or the buccal-lingual dimension formed by the tooth extensions. Furthermore, the step of setting the dental device can include creating anatomically correct papilla forms from contours in the teeth of the shell-like analogue.

BRIEF DESCRIPTION OF THE DRAWINGS

FIG. 2 is a bottom view along an incisal edge of an example of a shell-like analogue in accordance with an illustrative embodiment of the dental device and method of use thereof disclosed herein;

FIG. 3 is a front view of the shell-like analogue shown in FIG. 2;

FIG. 4 is a top view along a cervical edge of the shell-like analogue shown in FIG. 2;

FIG. 5 is a rear view of the shell-like analogue shown in FIG. 2;

FIGS. 6 and 7 are side views of the shell-like analogue shown in FIG. 2;

FIG. 8 is a cross-section view along line 8-8 of the shell-like analogue shown in FIG. 3;

FIG. 9 is a cross-section view along line 9-9 of the shell-like analogue shown in FIG. 3;

Figure 1:
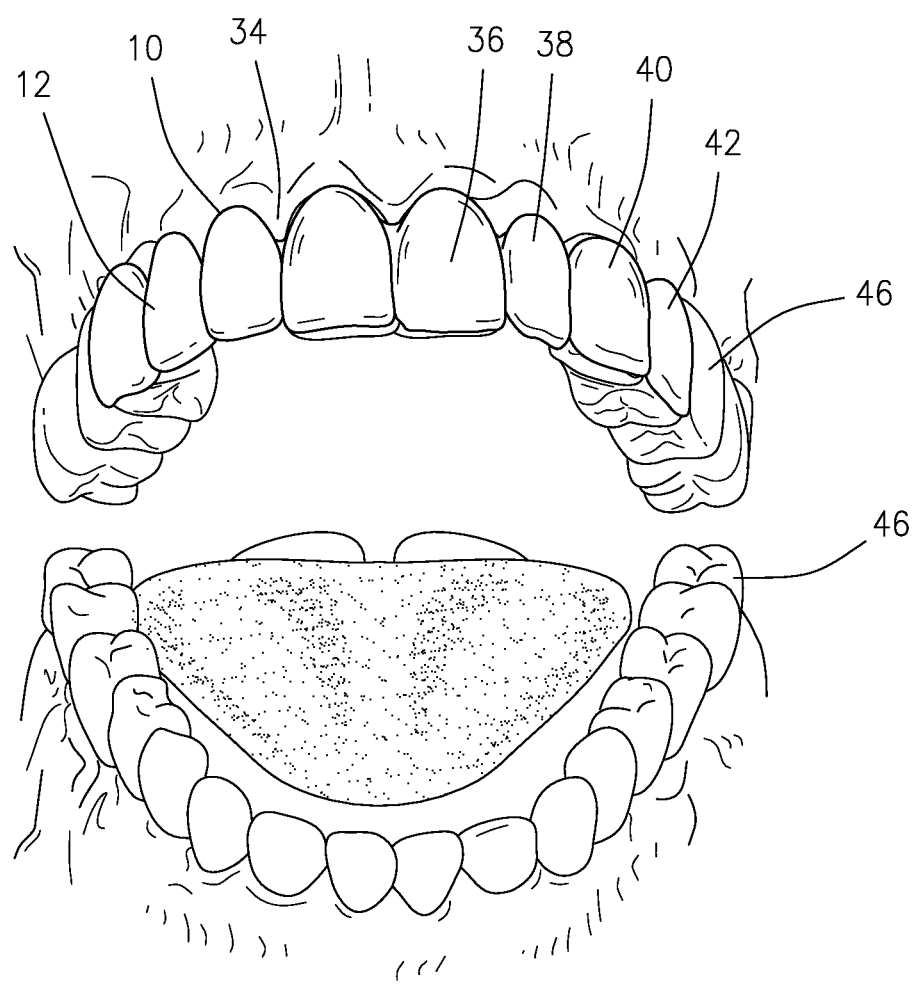
FIG. 1 is a perspective view of an example of a dental device temporarily affixed to the anterior maxillary teeth of a patient in accordance with an illustrative embodiment of the dental device and method of use thereof disclosed herein.

Other advantages and features will be apparent from the following description, and from the claims.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the construction and the arrangement of the structural and function details disclosed herein without departing from the spirit and scope of this disclosure. It is understood that the devices and methods are not limited to the embodiments set forth herein for purposes of exemplification.

Referring to the figures of the drawings, wherein like numerals of reference designate like elements throughout the several views, and initially to FIGS. 1 through 9, a unitary dental device 10 constructed from a suitable thermoplastic composition allowing the device to be heat molded by a dental practitioner sitting chair side to a patient. The dental device 10 is a single-piece, with each of the individual component parts discussed below and illustrated in the drawings being incorporated into the dental device 10. The dental device 10 includes a shell-like analogue 12 having the appearance of contoured, individual teeth 14. Between each of the individual teeth 14, a connection bridge 16 uniformly joins the proximal contact areas between adjacent teeth 14 to form the unitary shell-like analogue 12. The dental device 10 may be fabricated with either mandibular or maxillary teeth 14. Each tooth 14 includes a cervical edge 18 and an incisal edge 20, which form cervical embrasures 22 and incisal embrasures 24 of the shell-like analogue 12. Further, the shell-like analogue 12 may include a channel 26 generally spanning between an apical tip 28 and a distal tip 30 on a lingual surface 32 of each of the individual teeth 14. Additionally, the apical tip 28 of each of the individual teeth 14 of the shell-like analogue 12 may be further contoured so that the size of the cervical embrasure 22 spaces of the shell-like analogue 12 vary so as to be anatomically realistic and hygienically favorable. The contour of the teeth 14 of the dental device 10 permits the dental practitioner to fabricate papilla 34 in a denture base (not shown) that assists in retention and proper elimination of food debris in between each tooth 14. Moreover, individual teeth 14 having more or less curve may be utilized for female or male patients.

The dental device 10 includes at least anterior teeth 14, and as illustrated in FIGS. 1 through 5, the teeth 14 of the shell-like analogue 12 may characterize the central incisors 36, lateral incisors 38, canines 40, and first premolars 42. While the dental device 10 is illustrated as having eight (8) teeth, a greater or lesser number of teeth 14 may be employed within the spirit and scope of the dental device 10 and method of use thereof disclosed herein.

Figure 17A:
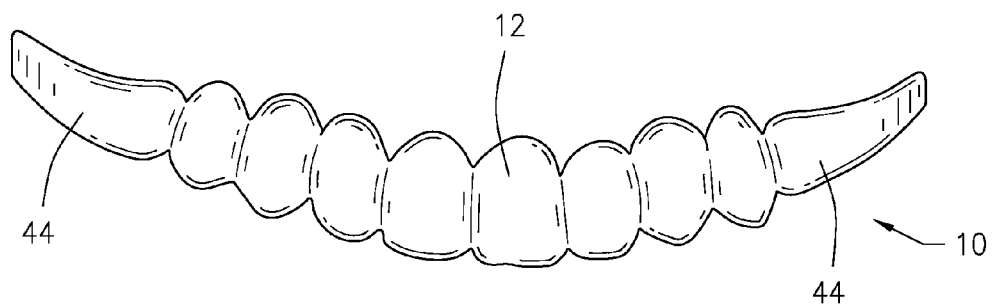
FIG. 17A is a front view of an example of a dental device having a pair of posterior tooth extensions in accordance with another illustrative embodiment of the dental device and method of use thereof disclosed herein.
Figure 17B:
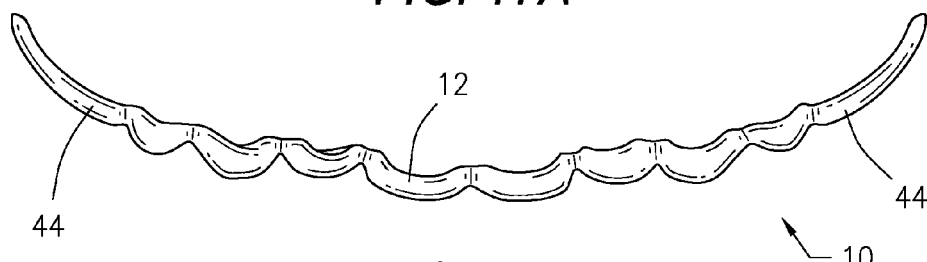
FIG. 17B is a top view along a cervical edge of the dental device shown in FIG. 17A.

The shell-like analogue 12 may also characterize posterior teeth 14, such as with individual second premolars and/or the molars (not shown), or as illustrated in FIGS. 17A and 17B with a pair of posterior tooth extensions or wings 44. Each of the tooth extensions 44 has a curvature and contour that follows and mimics the patient's posterior mandibular or maxillary teeth. The tooth extensions 44 permits the practitioner to create a custom buccal corridor specifically adapted for the individual patient. While sitting chair side, the dental practitioner may manipulate the tooth extensions 44 to position the posterior tooth by altering the anterior-posterior incline and/or the buccal-lingual dimension formed by the tooth extensions 44. The patient and the dental practitioner may visualize chair side the buccal corridor, allowing the posterior tooth to be positioned by manipulating the tooth extensions 44 to show more or less posterior tooth. The tooth extensions 44 are similarly constructed of the thermoplastic dental composition and are uniformly joined with the teeth 14 of the shell-like analogue 12 forming the dental device 10. The tooth extensions 44 may be heated using a suitable means and then manipulated chair side by the dental practitioner to fit the patient's buccal corridor. The dental device 10 having the shell-like analogue 12 of individual teeth 14 and tooth extensions 44 provides the patient and the dental practitioner with a preview of full mouth appearance prior to fabrication of the dental prosthesis, and guides the dental practitioner and/or the prosthetic technician in the orientation and placement of denture teeth for the dental prosthesis.

As illustrated in FIG. 1, the dental device 10 is sized such that it can be placed over existing teeth without causing the patient's lip to protrude unnaturally. As exemplified in the cross-sectional views of FIGS. 8 and 9, the dental device 10 may have a thickness of between approximately 0.02 inches and approximately 0.08 inches, in particular approximately 0.06 inches to approximately 0.08 inches thick. The shell-like analogue 12 may have a width of about 2.5 inches, while each of the posterior tooth extensions 44 may be about 0.5 inches wide. The dental device 10 may be fabricated in varying heights, and in general, the individual teeth 14 of the shell-like analogue 12 may have heights between approximately 0.3 inches and approximately 0.5 inches, while the tooth extensions 44 may have heights of approximately 0.25 inches. The foregoing dimensions are presented for illustrative purposes only and the dental device 10 should not be so limited. Those skilled in the art will appreciate that the foregoing dimensions may be increased or decreased by approximately 20% in order to provide varying tooth sizes.

The dental device may be fabricated from the thermoplastic material. The thermoplastic material is any dental- or medical-grade thermoplastic material suitable for use in the human mouth, namely polyethylene, polystyrene and/or polypropylene. The thermoplastic dental material may be approximately 70% to approximately 90% W/W polystyrene with 1,3-butadien-e polymer and approximately 10% to approximately 20% W/W polystyrene. Alternatively, the thermoplastic dental material may be at least 96% by weight of said polystyrene and no more than 3% by weight of a mineral oil. In addition, the thermoplastic dental material may include a suitable dental colorant compound.

The dental device 10 and method of use thereof allow both the dental practitioner and the patient to select a particular tooth mode, shape and size that most appropriately fits the patient's face. The dental device 10 may come in varying standard sizes, such as small, medium and large, to fit a variety of patients. As illustrated in FIG. 1, the dental practitioner would align the dental device 10 about the mid-line of the patient's teeth and face, and ensure the distal flips 30 of the teeth 14 of the dental device 10 are sufficiently large to create a proper gum to smile relation. The dental device 10 is suitable for use with any dental alterations, such as complete and partial dentures and in total crowning. The selection and characterization process of the method of using the dental device 10 is performed chair side, and may be appropriate for edentulous patients as well as for those patients who will be losing their teeth in the future.

Once the tooth mode and size is selected, the dental device 10 can be made pliable by heating to a temperature of about 100° F. to about 150° F., in particular about 140° F., such as in warm water or with a hot flame. Once sufficiently heated, the dental device 10 can be shaped by the chair side dental practitioner to the particular arch dimensions of the individual patient.

In addition to forming the dental arch, the dental practitioner can adjust each of the individual teeth 14 forward or back or side to side, can tip the teeth 14 outward or inward, and/or can overlap the teeth 14 to look more natural, if needed. In particular, each of the teeth 14 may be respectively adjusted horizontally, vertically and angularly by the chair side dental practitioner. In addition, the connection bridges 16 of the dental device 10 permit the dental practitioner to overlap, vertical discrepancies, horizontal discrepancies, diastemata, facial-lingual angular variation and/or mesial-distal angular variation of each of the teeth 14 with respect to each other while sitting chair side to the patient.

Moreover, the dental practitioner can adjust each of the tooth extensions 44 to create a custom buccal corridor specifically adapted for the individual patient. While sitting chair side, the dental practitioner would heat each of the tooth extensions 44 and manipulate the dental device 10 to alter the anterior-posterior incline and/or the buccal-lingual dimension of the tooth extensions 44. The patient and the dental practitioner visualize chair side the buccal corridor, allowing the posterior tooth to be accurately and satisfactorily positioned by manipulating the tooth extensions 44 to show more or less posterior tooth.

Referring now to FIGS. 10 through 16 illustrating examples of the dental device 10, the shell-like analogue 12 has been manipulated to change the characterization of the dental device 10 to fit individual patient features and to match the particular curvature of the patient's upper or lower jaw.

Figure 10A:
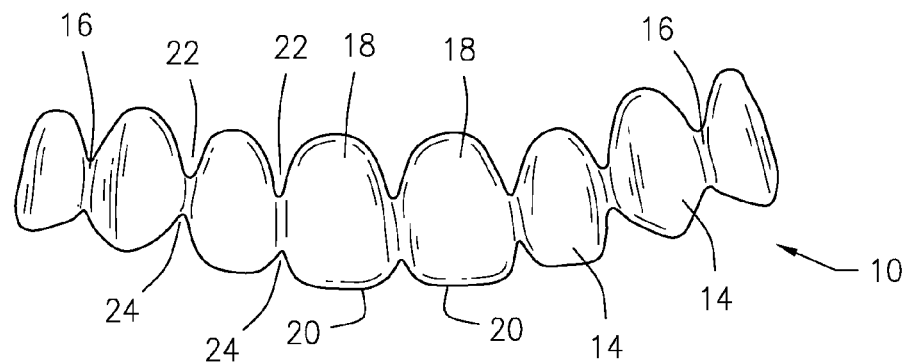
FIG. 10A is a perspective view of an example of the dental device wherein the shell-like analogue has been manipulated to change the characterization to fit an individual patient's features in accordance with an illustrative embodiment of the dental device and method of use thereof disclosed herein.
Figure 10B:
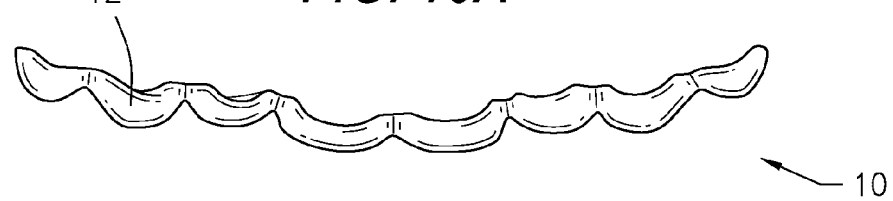
FIG. 10B is a bottom view along an incisal edge of the dental device shown in FIG. 10A.
Figure 11A:
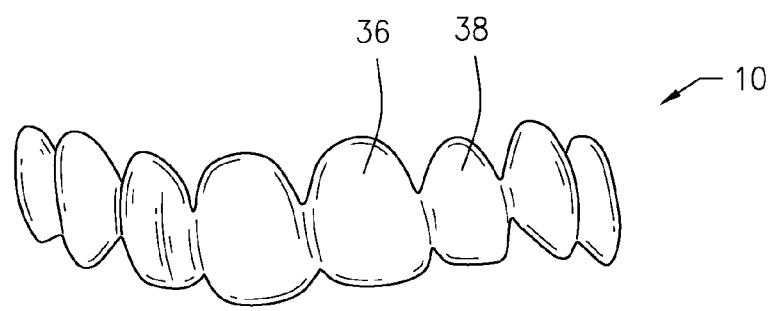
FIG. 11A is a perspective view of another example of the dental device wherein the shell-like analogue has been manipulated to change the characterization to fit an individual patient's features in accordance with an illustrative embodiment of the dental device and method of use thereof disclosed herein.
Figure 11B:
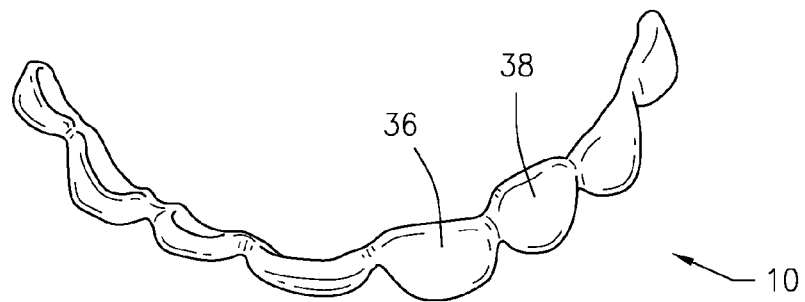
FIG. 11B is a bottom view along an incisal edge of the dental device shown in FIG. 11A.
Figure 12A:
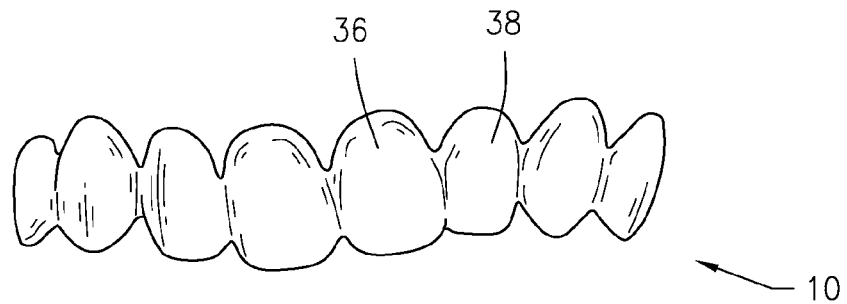
FIG. 12A is a perspective view of another example of the dental device wherein the shell-like analogue has been manipulated to change the characterization to fit an individual patient's features in accordance with an illustrative embodiment of the dental device and method of use thereof disclosed herein.
Figure 12B:
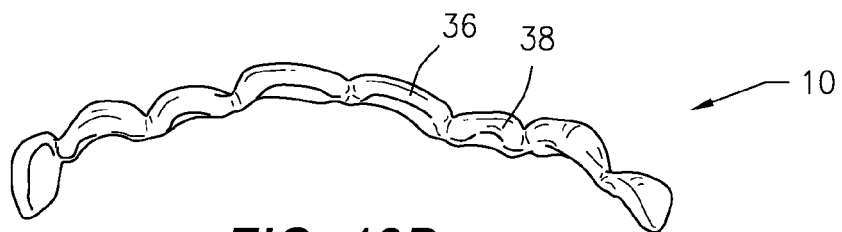
FIG. 12B is a bottom view along an incisal edge of the dental device shown in FIG. 12A.
Figure 13A:
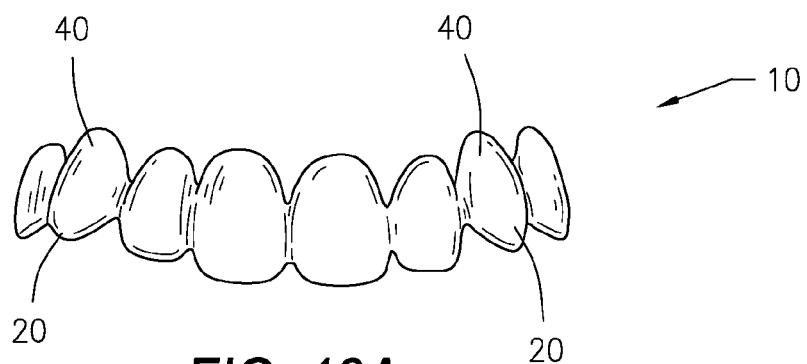
FIG. 13A is a perspective view of another example of the dental device wherein the shell-like analogue has been manipulated to change the characterization to fit an individual patient's features in accordance with an illustrative embodiment of the dental device and method of use thereof disclosed herein.
Figure 13B:
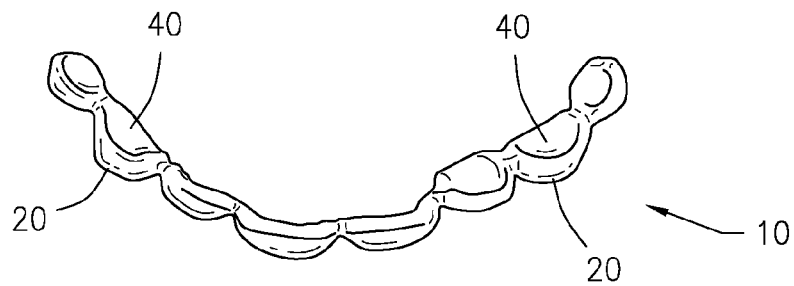
FIG. 13B is a bottom view along an incisal edge of the dental device shown in FIG. 13A.
Figure 14A:
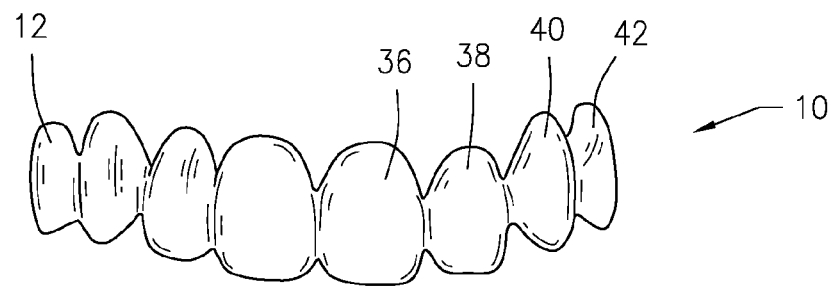
FIG. 14A is a perspective view of another example of the dental device wherein the shell-like analogue has been manipulated to change the characterization to fit an individual patient's features in accordance with an illustrative embodiment of the dental device and method of use thereof disclosed herein.
Figure 14B:
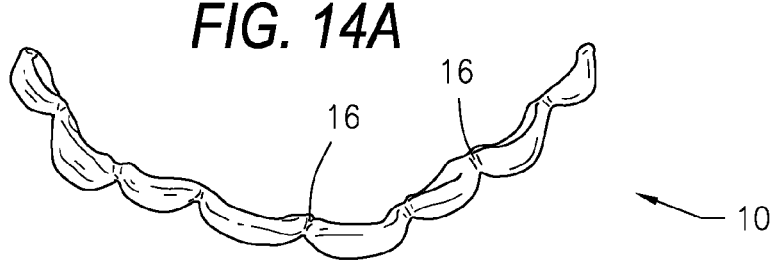
FIG. 14B is a bottom view along an incisal edge of the dental device shown in FIG. 14A.
Figure 15A:
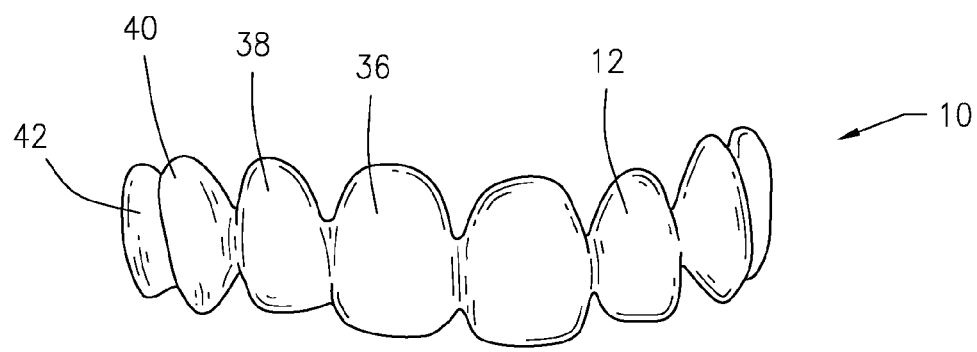
FIG. 15A is a perspective view of another example of the dental device wherein the shell-like analogue has been manipulated to change the characterization to fit an individual patient's features in accordance with an illustrative embodiment of the dental device and method of use thereof disclosed herein.
Figure 15B:
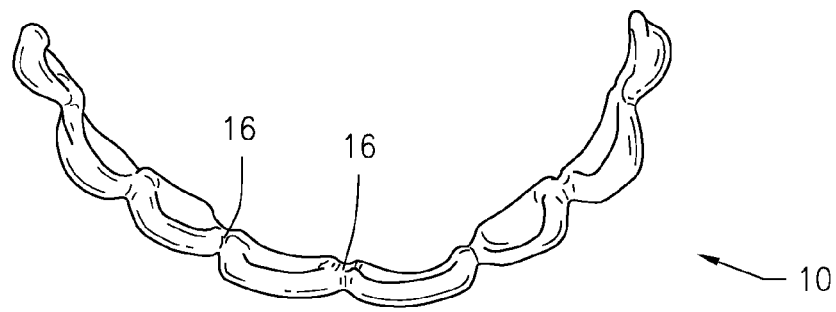
FIG. 15B is a bottom view along an incisal edge of the dental device shown in FIG. 15A.
Figure 16A:
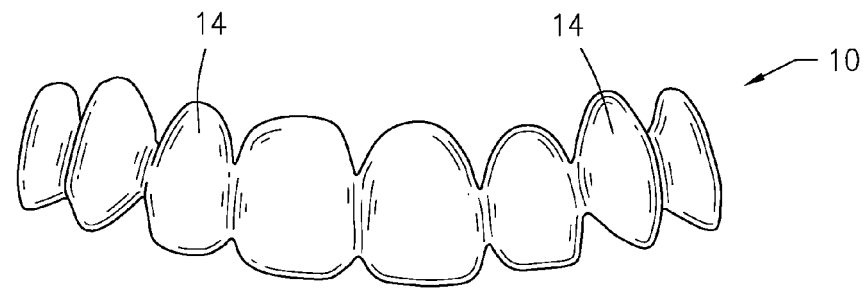
FIG. 16A is a perspective view of another example of the dental device wherein the shell-like analogue has been manipulated to change the characterization to fit an individual patient's features in accordance with an illustrative embodiment of the dental device and method of use thereof disclosed herein.
Figure 16B:
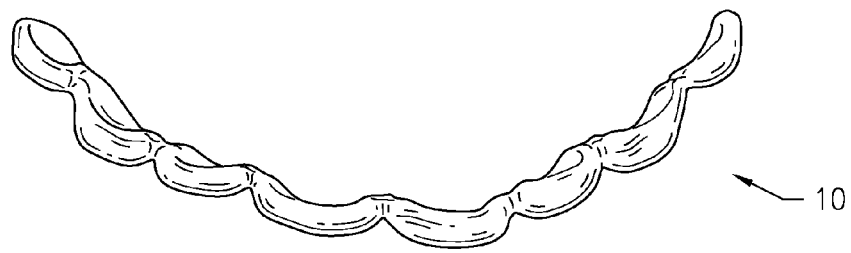
FIG. 16B is a bottom view along an incisal edge of the dental device shown in FIG. 11A.

FIGS. 10A and 10B generally illustrate the initial form of the dental device 10 prior to manipulation; as can be seen, the dental device 10 is manufactured to be generally straight, not yet having an arch. FIGS. 11A and 11B illustrate the dental device 10 having the central incisor 36 and the lateral incisor 38 rotated outwardly such that the lateral incisor 38 is tipped labially toward the patient's lip. Alternatively, the central 36 and lateral incisor 38 may be rotated inwardly such that the lateral incisor 38 is tipped lingually toward the patient's tongue or palate, as illustrated in FIGS. 12A and 12B. As seen in FIGS. 13A and 13B, the incisal edges 20 of the canine teeth 40 of the shell-like analogue 12 of the dental device 10 may be tipped outwardly toward the patient's lip forming a space or a gap between the lateral incisor 38 and the canine teeth 40 of the dental device 10. The dental device 10 illustrated in FIGS. 14A and 14B has been modified to have symmetrical appearance, while the dental device 10 illustrated in FIGS. 15A and 15B has a narrower arch than the dental device 10 illustrated in FIGS. 14A and 14B in order to fit a particular patient's dental ridge. Lastly, FIGS. 16A and 16B illustrate each of the dental arches having at least one tooth 14 that is manipulated outwardly to some degree. The dental device 10 and method of use thereof should not be limited to the manipulations exemplified in FIGS. 10 through 16, as those skilled in the art will readily appreciate that other manipulations are possible in order to characterize and fit the dental device 10 to a particular patient.

Returning now to FIG. 1, the dental device 10 may be temporarily affixed in the patient's mouth, such as by utilizing a small amount of dental wax (not shown) to adhere the dental device 10 to the patient's exiting dentation 46, allowing both the patient and the dental practitioner to visualize and observe (or "preview") chair side the look of a final smile design, including the buccal corridor, with a fully-fabricated dental prosthesis. Once the patient and practitioner are satisfied with the particular tooth arrangement and characterization, a suitable dental impression (not shown) can be made and then sent to the prosthetic technician to fabricate the final dental prosthesis.

Alternatively, the dental device 10 can be constructed of a suitable thermosetting dental composition. The thermosetting dental device 10 would have the same strength and wearibility as existing fabricated prosthetic teeth. Once the patient and dentist are satisfied with the particular tooth arrangement and characterization, the dental practitioner and/or the prosthetic technician can integrate the thermosetting dental device 10 into the final dental prosthesis.

The dental device 10 may be also further finished by refining, shaping and/or polishing using dental laboratory tools and prosthodontic techniques for both aesthetic (e.g., tooth shape, separation and definition) and functional (e.g., bite refinements, removing excess bulk to ensure patient comfort) purposes. In particular, once the patient is satisfied with the look, feel and function of the temporality affixed dental device 10, the dental practitioner makes a face bow transfer of the dental device 10, refines the esthetics of the dental device 10 and obtains a wax bite registration (not shown). After the wax bite registration is made, a working model is mounted on an articulator, using the face bow, and the dental device 10 is then seated on the working model (not shown). The wax bite registration is then positioned on the dental device 10 and the particular arch of the patient may be related using the wax bite registration. Once proper occlusion is accomplished, the working model and the dental device 10 may be removed from the articulator.

Furthermore, the dental device 10 and method of use thereof may be constructed such that the dental device 10 may be electronically scanned and then the teeth milled from the digital impression. The dental device 10 may be constructed of barium sulfate or coated with a suitable refractory material or spray material allowing the dental device 10 to be electronically scanned. The dental device can then be milled into an anatomically accurate composite shell-like analogue using CAD/CAM dental technologies.

Whereas, the devices and methods have been described in relation to the drawings and claims, it should be understood that other and further modifications, apart from those shown or suggested herein, may be made within the spirit and scope of this invention.

What is claimed is:

1. A dental device, comprising:
   a unitary, shell-like analogue having individual teeth unified with connection bridges joining only proximal contact areas of adjacent teeth, each of said teeth having a cervical edge and an incisal edge forming cervical embrasures and incisal embrasures intermediate of adjacent teeth, said cervical embrasures and said incisal embrasures being substantially free of said connection bridges; and
   said shell-like analogue constructed from a heat-moldable material comprising thermoplastic or thermosetting material that is pliable when heated to between 100° F. and 150° F. and is suitable for use in the human mouth, said thermoplastic or thermosetting material consisting essentially of about 70% to 90% W/W polystyrene with 1,3-butadiene polymer and about 10% to 20% W/W polystyrene, each of said teeth having a thickness of between approximately 0.020 inches and approximately 0.080 inches, each of said teeth having a height of between approximately 0.3 inches and approximately 0.5 inches, said shell-like analogue having a width of about 2.5 inches, each of said teeth being adjustable along said connection bridges for horizontal, vertical and angular adjustments with respect to each other by a chairside dental practitioner, each of said teeth being adjustable along said connection bridges for overlap, vertical discrepancies, horizontal discrepancies, diastemata, facial-lingual angular variation and/or mesial-distal angular variation of each of said teeth with respect to each other by said chairside dental practitioner.

2. The dental device of claim 1 wherein said shell-like analogue is pliable when heated to 140° F.

3. The dental device of claim 1 wherein said heat-moldable material further comprises a colorant compound.

4. The dental device of claim 1 wherein each of said teeth of shell-like analogue are contoured on a lingual portion.

5. The dental device of claim 1 wherein said lingual portion of each of said teeth having a channel generally spanning between an apical tip and a distal tip.

6. The dental device of claim 1 wherein said teeth of said shell-like analogue are selected from the group consisting of mandibular and/or maxillary teeth.

7. The dental device of claim 6 wherein said teeth of said shell-like analogue further comprise at least anterior teeth.

8. The dental device of claim 1 wherein said cervical embrasures of said shell-like analogue allows a denture base to have anatomically accurate papilla.

9. The dental device of claim 6 wherein said maxillary teeth are maxillary central incisors, maxillary lateral incisors, maxillary canines, and/or maxillary first premolars.

10. The dental device of claim 6 wherein said mandibular teeth are mandibular central incisors, mandibular lateral incisors, mandibular canines, and/or mandibular first premolars.

11. The dental device of claim 6 wherein said shell-like analogue further comprises at least one posterior tooth extension.

12. The dental device of claim 11 further comprising a pair of posterior tooth extensions having a curvature and contour mimicking posterior mandibular or maxillary teeth.

13. The device of claim 12 wherein each of said tooth extensions is adjustable along the anterior-posterior incline and/or the buccal-lingual dimension to form a custom buccal corridor specifically adaptable to an individual patient.

14. The dental device of claim 1 wherein said dental device contains barium sulfate.

15. The dental device of claim 12 wherein each of said tooth extensions has a width of about 0.5 inches.

16. The dental device of claim 12 wherein each of said tooth extensions has a height of about 0.25 inches.

17. A dental device, comprising:
a unitary, shell-like analogue having individual teeth unified with connection bridges joining only proximal contact areas of adjacent teeth, each of said teeth having a cervical edge and an incisal edge forming cervical embrasures and incisal embrasures intermediate of adjacent teeth, said cervical embrasures and said incisal embrasures being substantially free of said connection bridges; and
said shell-like analogue constructed from a heat-moldable material comprising thermoplastic or thermosetting material that is pliable when heated to between 100° F. and 150° F. and is suitable for use in the human mouth, said thermoplastic or thermosetting material consists essentially of at least 96% by weight of polystyrene and no more than 3% by weight of a mineral oil, each of said teeth being adjustable along said connection bridges for horizontal, vertical and angular adjustments with respect to each other by a chairside dental practitioner, each of said teeth being adjustable along said connection bridges for overlap, vertical discrepancies, horizontal discrepancies, diastemata, facial-lingual angular variation and/or mesial-distal angular variation of each of said teeth with respect to each other by said chairside dental practitioner.

18. The dental device of claim 17 further comprising each of said teeth having a thickness of between approximately 0.020 inches and approximately 0.080 inches, each of said teeth having a height of between approximately 0.3 inches and approximately 0.5 inches, and said shell-like analogue having a width of about 2.5 inches.

19. The dental device of claim 17 wherein said heat-moldable material further comprises a colorant compound.

20. The dental device of claim 17 wherein each of said teeth of shell-like analogue are contoured on a lingual portion.

21. The dental device of claim 20 wherein said lingual portion of each of said teeth having a channel generally spanning between an apical tip and a distal tip.

22. The dental device of claim 17 wherein said shell-like analogue further comprises at least one posterior tooth extension.

23. The dental device of claim 22 wherein each of said tooth extensions is adjustable along the anterior-posterior incline and/or the buccal-lingual dimension to form a custom buccal corridor specifically adaptable to an individual patient.

* * * * *